(12) United States Patent
Hendrikson

(10) Patent No.: US 8,114,116 B2
(45) Date of Patent: Feb. 14, 2012

(54) INTRODUCTION CATHETER SET FOR A SELF-EXPANDABLE IMPLANT

(75) Inventor: Per Hendrikson, Herlufmagle (DK)

(73) Assignee: Cook Medical Technologies LLC, Bloomington, IN (US)

( * ) Notice: Subject to any disclaimer, the term of this patent is extended or adjusted under 35 U.S.C. 154(b) by 918 days.

(21) Appl. No.: 12/009,542

(22) Filed: Jan. 18, 2008

(65) Prior Publication Data

US 2009/0187208 A1    Jul. 23, 2009

(51) Int. Cl.
*A61M 29/00* (2006.01)

(52) U.S. Cl. ........................................ 606/200; 606/213

(58) Field of Classification Search .................. 606/200, 606/213
See application file for complete search history.

(56) References Cited

U.S. PATENT DOCUMENTS

| | | |
|---|---|---|
| 3,334,629 A | 8/1967 | Cohn |
| 3,540,431 A | 11/1970 | Mobin-Uddin |
| 3,952,747 A | 4/1976 | Kimmell, Jr. |
| 4,425,908 A | 1/1984 | Simon |
| 4,619,246 A | 10/1986 | Molgaard-Nielsen et al. |
| 4,643,184 A | 2/1987 | Mobin-Uddin |
| 4,688,553 A | 8/1987 | Metals |
| 4,710,192 A | 12/1987 | Liotta et al. |
| 4,727,873 A | 3/1988 | Mobin-Uddin |
| 4,793,348 A | 12/1988 | Palmaz |
| 4,817,600 A | 4/1989 | Herms et al. |
| 4,832,055 A | 5/1989 | Palestrant |
| 4,936,823 A | 6/1990 | Colvin et al. |
| 4,943,297 A | 7/1990 | Saveliev et al. |
| 4,957,501 A | 9/1990 | Lahille et al. |
| 4,990,156 A | 2/1991 | Lefebvre |
| 5,147,379 A | 9/1992 | Sabbaghian et al. |
| 5,152,777 A | 10/1992 | Goldberg et al. |
| 5,217,484 A | 6/1993 | Marks |
| 5,300,086 A | 4/1994 | Gory et al. |
| 5,324,304 A | 6/1994 | Rasmussen |
| 5,344,427 A | 9/1994 | Cottenceau et al. |
| 5,417,708 A | 5/1995 | Hall et al. |
| 5,484,444 A | 1/1996 | Braunschweiler et al. |
| 5,562,698 A | 10/1996 | Parker |
| 5,601,568 A | 2/1997 | Chevillon et al. |
| 5,630,801 A | 5/1997 | Roussigne et al. |
| 5,634,942 A | 6/1997 | Chevillon et al. |
| 5,649,953 A | 7/1997 | Lefebvre |
| 5,681,347 A * | 10/1997 | Cathcart et al. ................ 606/200 |
| 5,683,451 A | 11/1997 | Lenker et al. |
| 5,702,419 A | 12/1997 | Berry et al. |
| 5,709,704 A | 1/1998 | Nott et al. |
| 5,725,550 A | 3/1998 | Nadal |
| 5,755,777 A | 5/1998 | Chuter |
| 5,755,790 A | 5/1998 | Chevillon et al. |

(Continued)

FOREIGN PATENT DOCUMENTS

EP    0430848 A1    11/1989

(Continued)

*Primary Examiner* — Tuan Nguyen
(74) *Attorney, Agent, or Firm* — Brinks Hofer Gilson & Lione

(57) ABSTRACT

The present invention discloses an introduction catheter set for a collapsible self-expandable implant into a blood vessel of a patient. The invention discloses in particular the introduction of collapsible self-expandable stents or filters of the type comprising a number of diverging legs to secure correct positioning of the implant when arranged in the blood vessel.

12 Claims, 5 Drawing Sheets

U.S. PATENT DOCUMENTS

| | | |
|---|---|---|
| 5,788,707 A | 8/1998 | Del Toro et al. |
| 5,800,457 A | 9/1998 | Gelbfish |
| 5,810,874 A | 9/1998 | Lefebvre |
| 5,853,420 A | 12/1998 | Chevillon et al. |
| 5,860,998 A | 1/1999 | Robinson et al. |
| 5,895,410 A | 4/1999 | Forber et al. |
| 5,902,334 A | 5/1999 | Dwyer et al. |
| 5,951,585 A | 9/1999 | Cathcart et al. |
| 5,976,172 A | 11/1999 | Homsma et al. |
| 6,007,557 A | 12/1999 | Ambrisco et al. |
| 6,077,297 A | 6/2000 | Robinson et al. |
| 6,086,605 A | 7/2000 | Barbut et al. |
| 6,099,549 A | 8/2000 | Bosma et al. |
| 6,156,055 A | 12/2000 | Ravenscroft |
| 6,165,179 A | 12/2000 | Cathcart et al. |
| 6,193,739 B1 | 2/2001 | Chevillon et al. |
| 6,231,589 B1 | 5/2001 | Wessman et al. |
| 6,245,012 B1 | 6/2001 | Kleshinski |
| 6,254,609 B1 | 7/2001 | Vrba et al. |
| 6,258,026 B1 | 7/2001 | Ravenscroft et al. |
| 6,267,776 B1 | 7/2001 | O'Connell |
| 6,328,755 B1 | 12/2001 | Marshall |
| 6,342,062 B1 | 1/2002 | Suon et al. |
| 6,371,971 B1 | 4/2002 | Tsugita et al. |
| 6,383,193 B1 | 5/2002 | Cathcart et al. |
| 6,391,051 B2 | 5/2002 | Sullivan, III et al. |
| 6,395,017 B1 | 5/2002 | Dwyer et al. |
| 6,436,120 B1 | 8/2002 | Meglin |
| 6,440,077 B1 | 8/2002 | Jung et al. |
| 6,506,205 B2 | 1/2003 | Goldberg et al. |
| 6,517,559 B1 | 2/2003 | O'Connell |
| 6,602,273 B2 | 8/2003 | Marshall |
| 6,623,506 B2 | 9/2003 | McGuckin, Jr. et al. |
| 6,623,518 B2 | 9/2003 | Thompson et al. |
| 6,652,557 B1 | 11/2003 | MacDonald |
| 6,706,054 B2 | 3/2004 | Wessman et al. |
| 6,726,621 B2 | 4/2004 | Suon et al. |
| 6,736,839 B2 | 5/2004 | Cummings |
| 6,773,448 B2 | 8/2004 | Kusleika et al. |
| 6,793,666 B2 | 9/2004 | Hansen et al. |
| 6,837,898 B2 | 1/2005 | Boyle et al. |
| 6,878,153 B2 | 4/2005 | Linder et al. |
| 6,887,256 B2 | 5/2005 | Gilson et al. |
| 6,939,361 B1 | 9/2005 | Kleshinski |
| 6,951,570 B2 | 10/2005 | Linder et al. |
| 6,958,074 B2 | 10/2005 | Russell |
| 6,962,598 B2 | 11/2005 | Linder et al. |
| 6,991,641 B2 | 1/2006 | Diaz et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,001,424 B2 | 2/2006 | Patel et al. |
| 7,033,376 B2 | 4/2006 | Tsukernik |
| 7,048,752 B2 | 5/2006 | Mazzocchi et al. |
| 7,056,286 B2 | 6/2006 | Ravenscroft et al. |
| 7,147,649 B2 | 12/2006 | Thomas |
| 2002/0138097 A1 | 9/2002 | Ostrovsky et al. |
| 2002/0151952 A1 | 10/2002 | Perouse |
| 2003/0004537 A1 | 1/2003 | Boyle et al. |
| 2003/0114880 A1 | 6/2003 | Hansen |
| 2003/0144670 A1 | 7/2003 | Pavcnik et al. |
| 2003/0176888 A1 | 9/2003 | O'Connell |
| 2004/0006361 A1 | 1/2004 | Boyle et al. |
| 2004/0082966 A1 | 4/2004 | WasDyke |
| 2004/0088001 A1 | 5/2004 | Bosma et al. |
| 2004/0116938 A1 | 6/2004 | Forber et al. |
| 2005/0010247 A1 | 1/2005 | Kusleika et al. |
| 2005/0043757 A1 | 2/2005 | Arad et al. |
| 2005/0101982 A1 | 5/2005 | Ravenscroft et al. |
| 2005/0113862 A1 | 5/2005 | Besselink et al. |
| 2005/0131451 A1 | 6/2005 | Kleshinski et al. |
| 2005/0182439 A1 | 8/2005 | Lowe |
| 2005/0222604 A1 | 10/2005 | Schaeffer |
| 2005/0234503 A1 | 10/2005 | Ravenscroft et al. |
| 2005/0267512 A1 | 12/2005 | Osborne et al. |
| 2005/0283185 A1 | 12/2005 | Linder et al. |
| 2006/0009798 A1 | 1/2006 | Callister et al. |
| 2006/0015141 A1 | 1/2006 | Linder et al. |
| 2006/0030875 A1 | 2/2006 | Tessmer |
| 2006/0041271 A1 | 2/2006 | Bosma et al. |
| 2006/0089664 A1 | 4/2006 | Hansen et al. |
| 2006/0089665 A1 | 4/2006 | Eskuri et al. |
| 2006/0089666 A1 | 4/2006 | Linder et al. |
| 2006/0100660 A1 | 5/2006 | Osborne et al. |
| 2006/0106417 A1 | 5/2006 | Tessmer et al. |
| 2006/0184193 A1 | 8/2006 | Lowe et al. |

FOREIGN PATENT DOCUMENTS

| | | |
|---|---|---|
| EP | 1734896 B1 | 4/2005 |
| WO | WO 2005/102212 | 11/2005 |
| WO | WO 2005/102213 | 11/2005 |
| WO | WO 2005/102214 | 11/2005 |
| WO | WO 2006/036867 | 4/2006 |

* cited by examiner

INTRODUCTION CATHETER SET FOR A SELF-EXPANDABLE IMPLANT

TECHNICAL FIELD

The present invention relates to an introduction catheter set for a collapsible self-expandable implant into a blood vessel of a patient.

Without being limited thereto the invention is concerned in particular with the introduction of collapsible self-expandable stents or filters of the type comprising a number of diverging legs to secure correct positioning of the implant when arranged in the blood vessel.

BACKGROUND OF THE INVENTION

Filters of the above-mentioned type are used, i.e. for permanent or temporary implantation in the vena cava, in particular the inferior vena cava, to prevent thrombi or emboli from reaching the patient's lungs and causing pulmonary embolization.

Such filters are well known in the art, e.g. from U.S. Pat. Nos. 3,952,747, 4,425,908; 4,619,246 and 5,324,304 as well as published European patent application No. 430848.

SUMMARY OF THE INVENTION

According to the invention an introduction catheter set is provided for introducing a collapsible, self-expandable implant, e.g. a filter for entrapping thrombi or emboli into a blood vessel of a patient, said implant being of the type comprising a number of diverging spring-biased anchoring legs to centre the implant in respect of the blood flow through said vessel, said catheter set comprising a flexible external guide sheath, a flexible internal catheter having a tubular end member at its distal end and being slidably displaceable inside said guide sheath to a position in which said tubular end member protrudes from the distal end of said sheath, and a retaining member slidably arranged in said tubular end member for releasably retaining the anchoring legs of the implant in defined angular positions in respect of each other, said retaining member being connected with a flexible displacement member extending throughout the internal catheter, the proximal ends of said displacement member and the internal catheter being connected with a first and a second operating member, respectively, by operation of which said retaining member is displaceable in respect of said tubular end member from a retaining position, in which the anchoring legs of the implant are inside said tubular end member, to a release position, in which the retaining member protrudes from the tubular end to release the anchoring legs of the implant.

In use of this catheter set the internal catheter and the flexible displacement member surrounded by it with the implant attached to the retaining member is first slidably guided through the external sheath to the desired location in a blood vessel, such as the inferior vena cava to a position in which the implant and the distal end of internal catheter protrudes from the distal end of the external sheath. In this position the ends of the anchoring legs are still retained in place inside the tubular end member of the internal catheter. By retraction of the internal catheter in respect of the displacement member, the retaining member gets clear of the tubular end member towards the position from which the anchoring legs are released and expanded as a result of their natural spring-bias.

The retaining member comprises a cylindrical piston having a plurality of slits extending radially inward from the outer cylindrical surface of the piston and extending axially from the distal end of the piston adjacent to the filter and to the proximal end of the piston remote from the filter, the slits being circumferentially spaced one from another around the piston and each being adapted to receive a respective anchoring leg of the filter. The slits at their respective proximal ends each communicate with an internal void in the piston so that an anchoring leg received in a respective slit may make contact with at least one other anchoring leg in the internal void.

The introduction catheter set according to the invention secures a maximum control of the implant during introduction and advancement to the intended place of implantation in a blood vessel until actual release of the anchoring legs.

Moreover, since the only rigid members of the catheter set are the tubular end member of the internal catheter and the retaining member which during introduction are axially inside the tubular end member and both members may have a short axial length, maximum flexibility is obtained compared to prior art insertion instruments.

The retention of the anchoring legs in defined angular positions in respect of each other corresponding to the angular separation of the legs in the implant itself until the moment of release effectively prevents the anchoring legs from intermeshing with one another and contributes to facilitate the implantation.

The internal void in the retaining member, enabling an anchoring leg received in a respective slit to make contact at least one other anchoring leg in the internal void, leads to a significant reduction in the profile of the assembly.

It is desirable to provide hooks at the free ends of the anchoring legs to penetrate into the vessel wall when the filter is deployed at a delivery location in the blood vessel. If these hooks are of insufficient radial extent, they may fail to exert a sufficient anchoring force to prevent displacement of the filter from its correct operating position or—still worse—may fail to prevent the filter from being swept from the working site. However, in the collapsed delivery configuration, it is the radial extent of these hooks that places a lower limit on the profile of the assembly and on the diameter of the delivery sheath. By minimising the diameter of the delivery assembly at the location of the hooks, the present invention permits a significant reduction in this profile, in one example from a minimum diameter of 8.5 French to 7 French.

BRIEF DESCRIPTION OF THE DRAWINGS

In the following the invention will be further explained with reference to the accompanying drawings in which.

Figure 1:
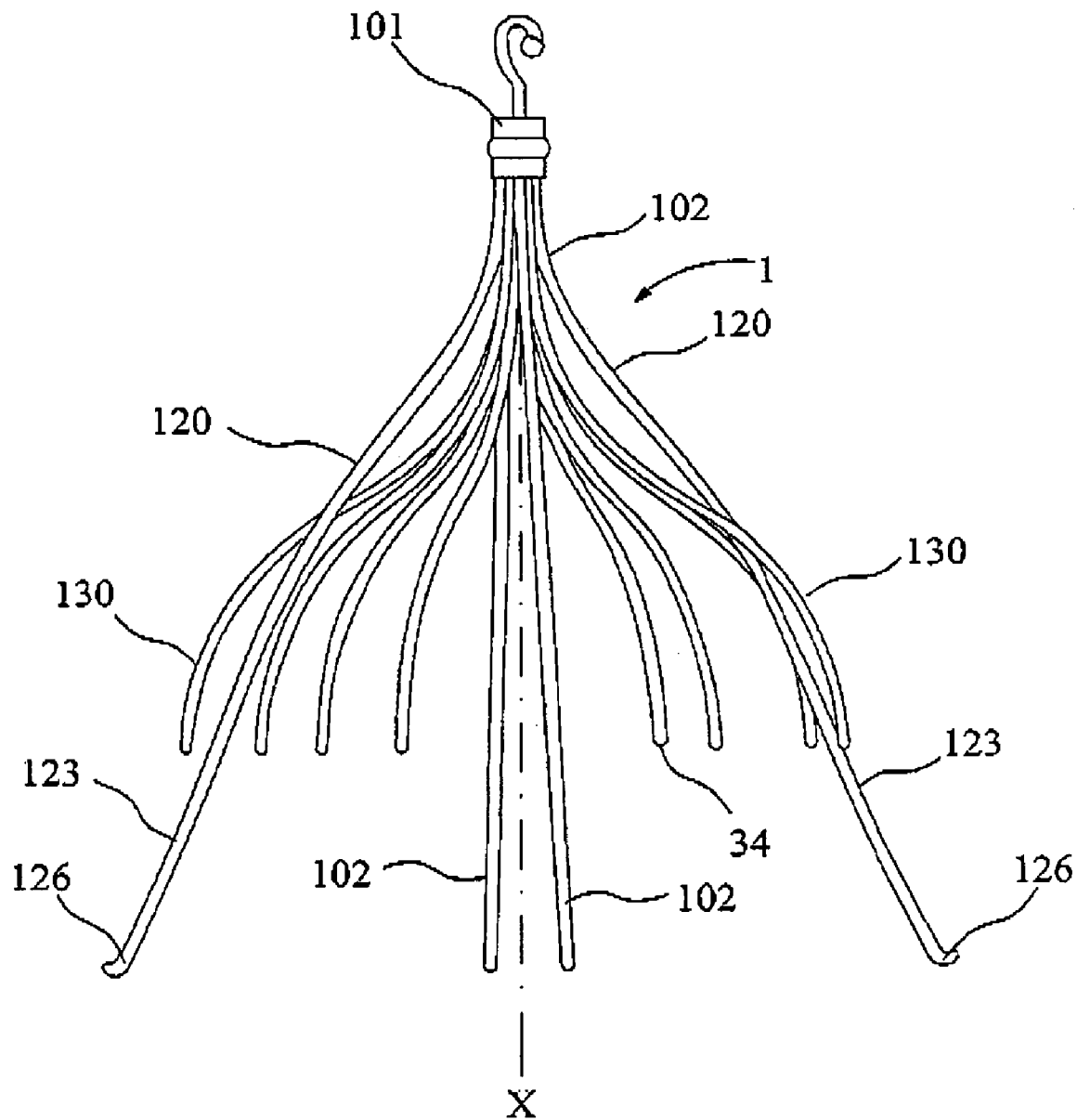
FIG. 1 shows a known vena cava filter suitable for use with the present invention.

The embodiment of the introduction catheter set of the invention illustrated in the drawings is intended for implantation of a collapsible vena cava filter of the kind discussed in EP-A-1 734 896; EP-A-1 737 383; EP-A-1 737 384; EP-A-1 737 385; or EP-A-1 802 252.

An example of such a filter is shown in FIG. 1. This illustrates a collapsible vena cava filter 1 in an expanded state and comprising four primary struts 102 extending from a hub 101. Hub 101 attaches by crimping first ends of primary struts 102 together in a compact bundle along a central or longitudinal axis X of the filter. The hub 101 has a minimal diameter for the size of wire used to form the struts.

The primary struts 102 may be formed of a superelastic material, stainless steel wire, Nitinol, cobalt-chromium-nickel-molybdenum-iron alloy, or cobalt chrome-alloy or any other suitable superelastic material that will result in a self-opening or self-expanding filter. The primary struts 102 may be formed from wire having a round cross-section with a diameter of at least about 0.6 microns (0.015 inches).

Each primary strut 102 includes a first curved portion 120 that is configured to softly bend away from the longitudinal or central axis X of the filter 1 and a second curved portion 123 that is configured to softly bend toward the longitudinal axis of the filter 1. The primary struts 102 may comprise a straight segment of about 5 mm for anchoring in the hub 101. The length of the first curved portion 120 could be about 8-12 mm and the radius of curvature about 60-80 mm. The length of the second curved portion 123 could be 8-15 mm and the radius of curvature about 40-60 mm. Due to the soft bends a prominence or a point of inflection on the primary strut 102 is substantially avoided to aid in non-traumatically engaging the vessel wall.

The primary struts 102 terminate at anchoring hooks 126 that will anchor in the vessel wall when the filter 1 is deployed at a delivery location in the blood vessel. The primary struts 102 are configured to move between an expanded state for engaging the anchoring hooks 126 with the blood vessel and a collapsed state for filter retrieval or delivery.

The filter 1 includes a plurality of secondary struts 130 also extending from hub 101. Each primary strut 102 has two secondary struts 130 in side-by-side relationship with the primary strut 102. The secondary struts 130 serve to centralize the filter 1 in the expanded state in the blood vessel. The secondary struts 130 may be made from the same type of material as the primary struts 102. However, the secondary struts 130 may have a smaller diameter.

Figure 2:
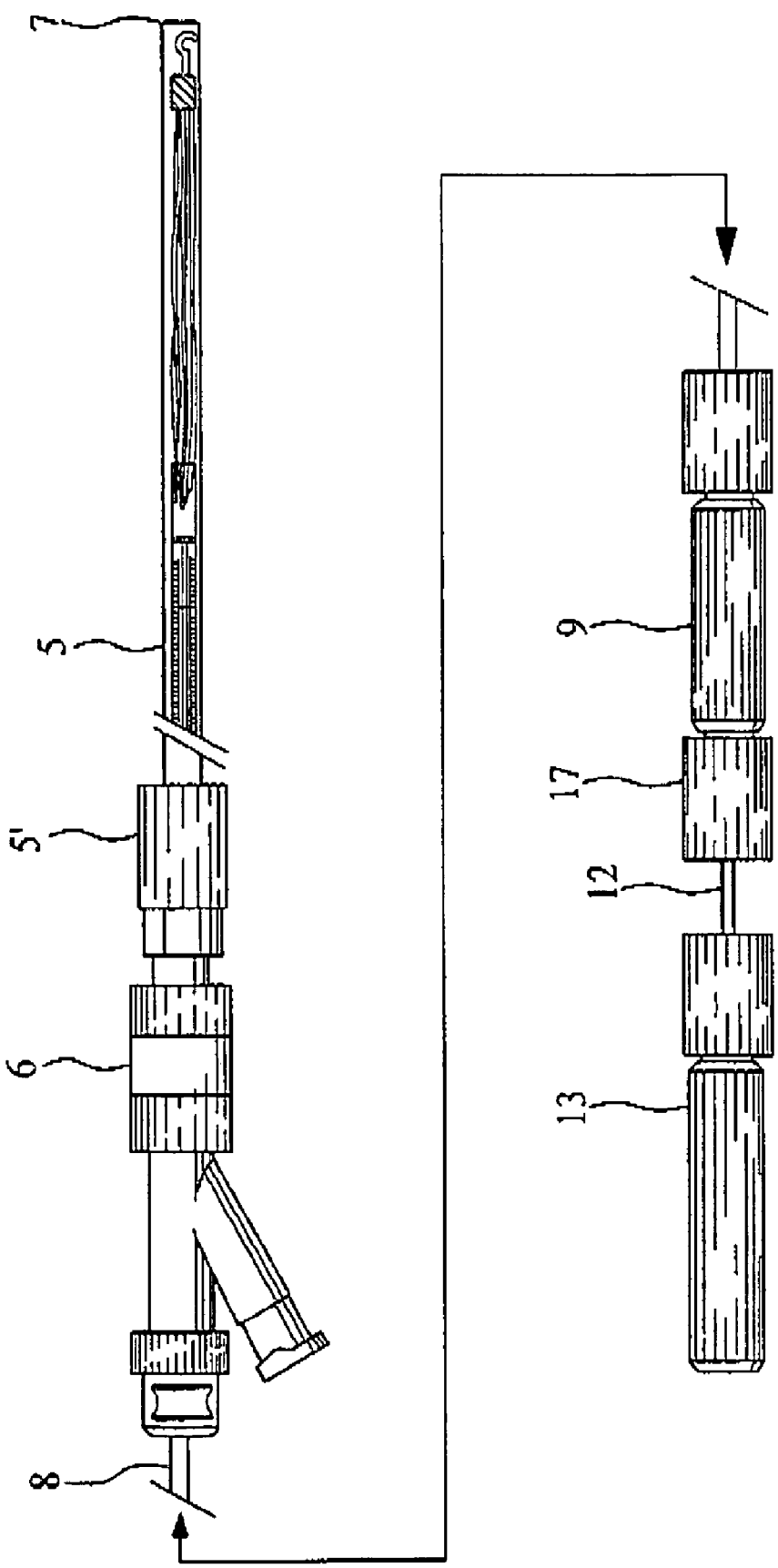
FIG. 2 is a general view of an embodiment of an introduction catheter set according to the invention.

As shown in FIG. 2, the introduction catheter set comprises a flexible external guide sheath 5 secured at its proximal end by means of a hub member 5' to a side-arm adapter 6 which may be of the so-called Tuohy-Borst type, whereas the guide sheath 5 has an open distal end 7.

A flexible internal filter catheter 8 is slidably displaceable inside the guide sheath 5 and is connected at its proximal end with an operating member 9 serving to push the filter catheter 8 through the external guide sheath 5. At its distal end the flexible internal catheter 8 is connected with a tubular end member 10.

Slidably arranged inside the tubular end member 10 is a filter retaining member 11 serving to releasably retain the anchoring hooks 126 of the primary struts 102 of the filter 1 inside the tubular end member 10 until the introduction catheter set has been advanced through the veins of the patient to the intended place of implantation such as the vena cava.

The retaining member 11 is connected with an elongate flexible displacement member 12 such as a wire member extending throughout the length of the internal catheter 8 and being connected at its opposite proximal end with an operating member 13.

Figure 3:
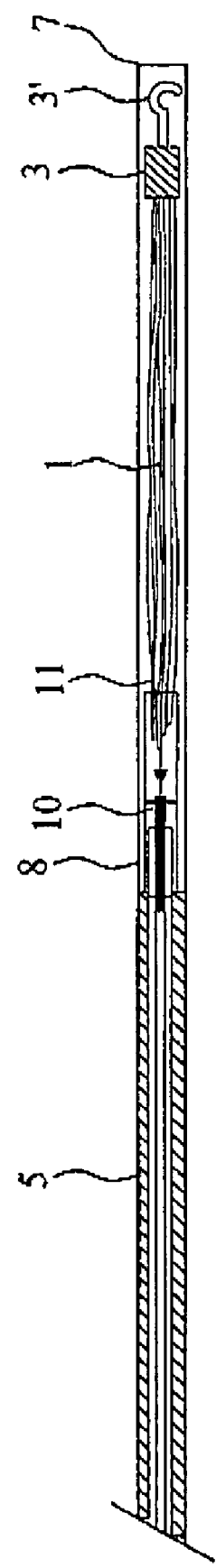
FIG. 3 is an enlarged view of the distal end view of the catheter set.
Figure 4:
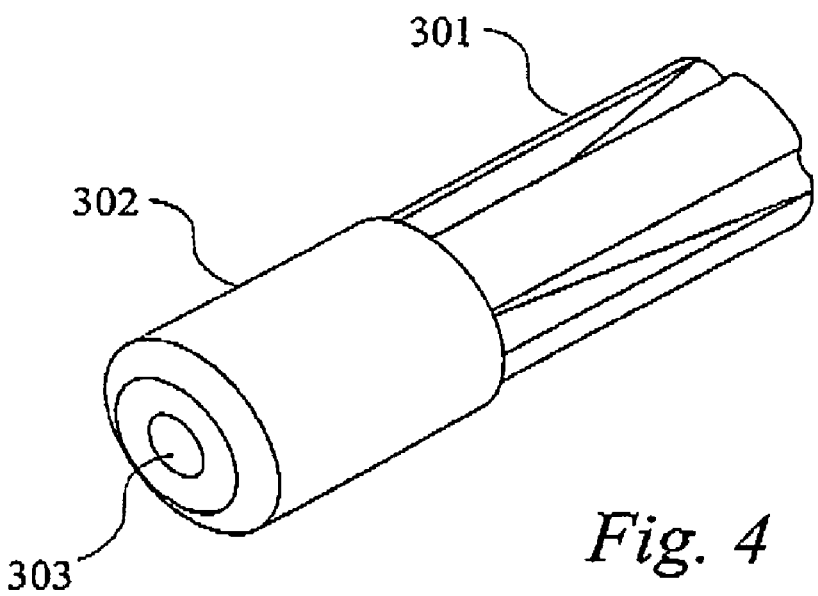
FIG. 4 is a perspective view of an embodiment of the filter retaining member.
Figure 5:
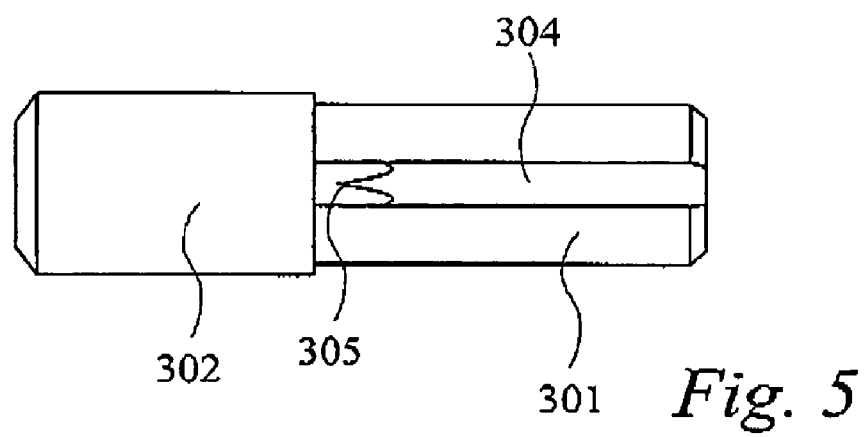
FIG. 5 is a side elevation of the filter retaining member of FIG. 4.
Figure 6:
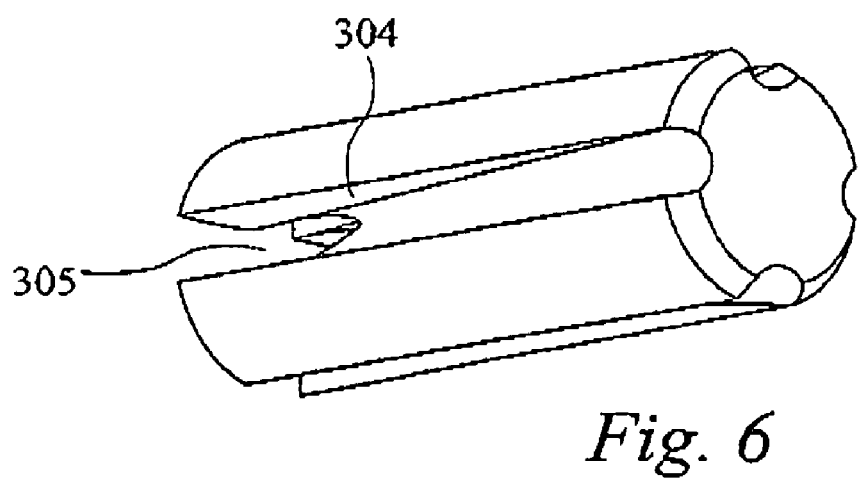
FIG. 6 is an enlarged perspective view of part of the filter retaining member of FIG. 4.
Figure 7:
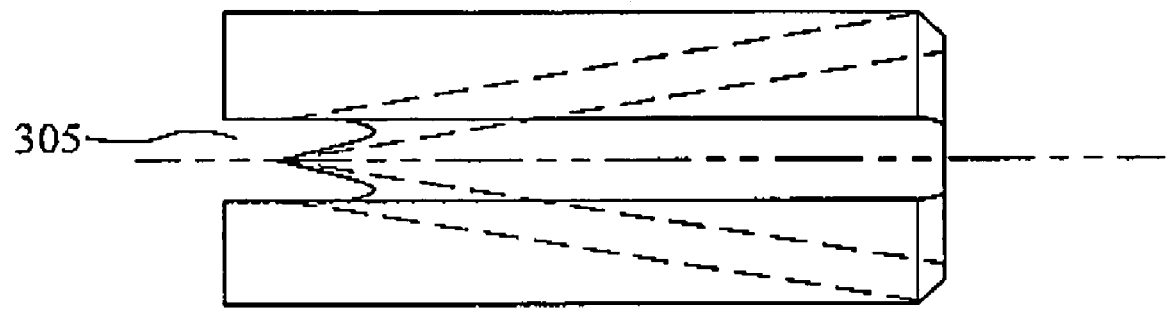
FIG. 7 is a side elevation of the part shown in FIG. 6.
Figure 8:
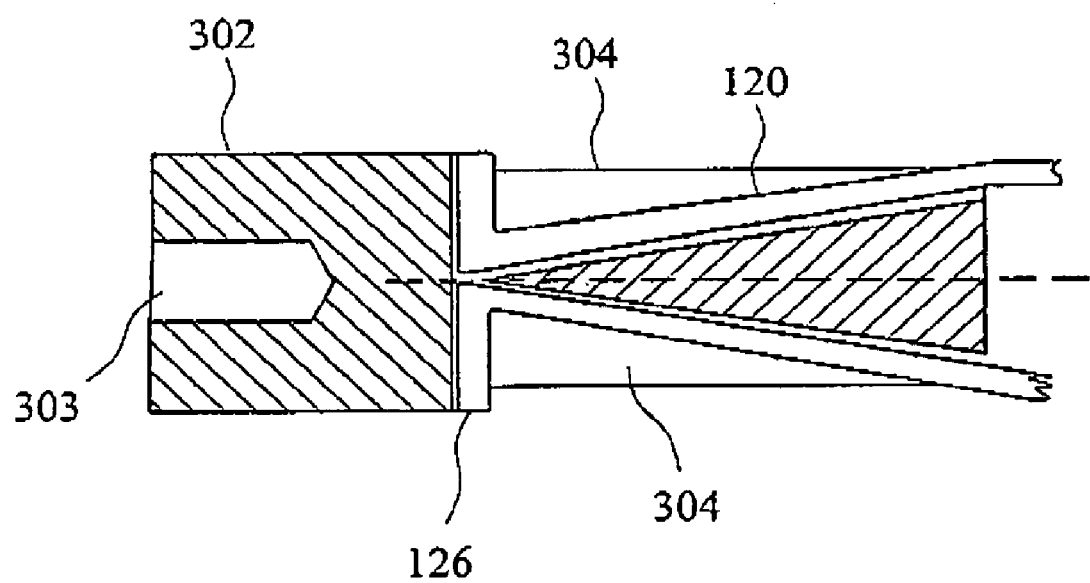
FIG. 8 is a section through the filter retaining member illustrating the engagement with the legs of the filter.

As illustrated in FIG. 3 which is an enlarged view of the distal end portion of the catheter in the introduction condition, the tubular end member 10 of the internal catheter 8 is retracted from the distal end 7 of the external guide sheath 5 over a distance permitting the filter 1 in its collapsed state to be inside the external guide sheath 5. In this condition the retaining member 11 is also retracted inside the tubular end member 10 to retain the free ends of the filter primary struts 102 safely inside the tubular end member 10.

This retaining position of the retaining member 11 is accomplished by safe-guarding corresponding relative positions of operating members 9 and 13 connected with the internal catheter 8 and the displacement member 12, respectively by spring bias means which may be incorporated in a manner not illustrated in operating member 9.

Moreover, in a manner known per se the adapter device 6 may have releasable arresting means for locking the internal catheter 8 in the relative position in respect of the external guide sheath 5 illustrated in FIG. 3.

As shown in FIGS. 4 to 8, the retaining member 11 may be formed as a piston 301 extending axially from a cylindrical mounting section 302. The piston 301 and the mounting section 302 are preferably machined separately from metal parts, typically stainless steel, and then laser welded or otherwise bonded together. A particularly preferred machining technique is EDM, especially wire EDM. The mounting section 302 has an external diameter which is slightly in excess (for example around 10%) of that of the piston 301. The mounting section has, at the end remote from the piston 301, a blind bore 303 to receive the distal end of wire member 12.

The piston 301 is provided with four longitudinal slits 304 corresponding with and adapted to receive the hooked free end of the respective four primary struts 102. The four slits 304 are equiangularly spaced about the circumference of the piston 301 and each has a radial depth that increases from the distal end of the piston 301 in a direction toward the mounting section 302. Critically, this increase in depth is configured such that the four slits 304 intersect one with another to form an internal void 305 within the piston 301. This means that—taking for example two diametrically opposed primary struts 102—the hooks 126 at the respective free ends of the primary struts which will be received in diametrically opposed slits 304, are able to touch one another. Typically the primary struts will be configured so that the hooks 126 are directed radially outward in this configuration so that the respective heels of the two hooks are capable of being brought into contact.

By this provision of an internal void, the profile of the collapsed free ends of the primary struts is thus brought to a minimum diameter. This minimum diameter may be regarded as—essentially—twice the radial length of the hooks. In the design of the retaining member, the external diameter of the mounting section 302 is chosen to be approximately equal to this minimum diameter, in one example exceeding the minimum diameter by a small clearance. The retaining member may then fit with a small clearance in respect of the tubular end member 10 of the internal catheter 8.

By displacement of the retaining member 11 in the direction out of the distal end of the tubular end member 10 by bringing operating members 9 and 13 into end-by-end contact, the retaining member 11 will be moved to a release position, in which it projects sufficiently outside the distal end of the tubular end member 10 to effect release and expansion of the anchoring legs 126 as a result of their inherent spring bias.

In actual use the introduction catheter set according to the invention may be supplied as two components, namely the external guide sheath 5 with the hub member 5' and a loading catheter system, comprising the internal catheter 8 with its operating member 9 and tubular end member 10 and arranged inside the latter, the retaining member 11 with its wire-shaped displacement member 12 and operating member 13. The side arm adapter 6 is slidably arranged on the internal catheter on the distal side of the operating member 9.

In the supply condition, the filter 1 is mounted in the tubular end member 10 by means of the retaining member 11 with the filter body projecting outside the tubular end member and covered by a peal-away sheath.

In operation the external guide sheath 5 is first advanced, following puncture of the femoral vein, e.g. by using the Seldinger technique, by use of a wire guide as know in the art to a desired place of implantation, which in this case may be in the inferior vena cava just below the renal veins.

The distal end of the internal catheter 8 with the projecting filter 1 covered by the abovementioned peal-away sheath is now advanced somewhat into the proximal end of the external guide sheath, and the peal-away sheath is removed. Thereafter, the side arm adapter 6 is displaced on the internal catheter 8 to get into connection with the hub member 5' of the external guide sheath.

The internal catheter 8 together with the wire member 12 arranged therein is now advanced in the external guide sheath 5 until the position shown in FIGS. 2 and 3, where a retrieval hook at the hub member 101 of the filter 1 coincides with the distal end 7 of the external guide sheath 5.

After verification of the position of implantation by means of X-ray examination, the side arm adapter 6 and with it the external guide sheath 5 is now retracted over the internal catheter 8 to a position which the filter is pre-released with its body portion getting clear of the external guide sheath 5 and slightly expanded, but still with the free ends of the anchoring legs 120 retained inside the tubular end member 10 by means of the retaining member 11.

In this condition, moderate repositioning of the filter is still possible, but in the embodiment shown the filter cannot be pulled back into the external guide sheath 5 due to its shape. Proper positioning can again be verified by X-ray examination.

In the pre-release position the tubular end member 10 projects with its distal end somewhat outside the distal end 7 of the external guide sheath 5. The side arm adapter 6 is secured relative to the internal catheter 8.

Whereas in the introduction stages described above, the operating members 9 and 13 have assumed mutually locked positions, e.g. by securing the operating member 9 to the wire member 12 by means of an arresting hub 17, the latter is now turned loose to permit retraction of operating member 9 towards operating member 13, whereby the retaining member 11 gets clear of the tubular end member 10 over a length slightly exceeding the length of the slits 304 in the retaining member 11.

Due to the spring bias of the anchoring legs 120, the filter 1 will now be completely released and assume the desired position of implantation with great accuracy, in which the filter is fixed in the vena cava by being anchored in respect of the vein wall by means of the bent hook ends of the anchoring legs 120.

The application of the filter set according to the invention is in no way limited to implantation of the specific form of a vena cava filter described in the foregoing and illustrated in the Figures but may with the same advantages extend to other types of implantation filters or stents and similar implants to be positioned in a blood vessel and having projecting anchoring legs.

The invention claimed is:

1. An introduction catheter set for introducing a collapsible, self-expandable implant, said implant being of the type comprising a number of diverging spring-biased anchoring legs to centre the implant in respect of the blood flow through said vessel, the anchoring legs having free ends for engaging said vessel, said catheter set comprising a flexible external guide sheath, a flexible internal catheter having a tubular end member at its distal end and being slidably displaceable inside said guide sheath to a position in which said tubular end member protrudes from the distal end of said sheath, and a retaining member slidably arranged in said tubular end member for releasably retaining the free ends of the anchoring legs of the implant in defined angular positions in respect of each other, said retaining member being connected with a flexible displacement member extending throughout the internal catheter, the proximal ends of said displacement member and the internal catheter being connected with a first and a second operating member, respectively, by operation of which said retaining member is displaceable in respect of said tubular end member from a retaining position, in which the anchoring legs of the implant are inside said tubular end member, to a release position, in which the retaining member protrudes from the tubular end member to release the anchoring legs of the implant, wherein the retaining member comprises a cylindrical piston having a plurality of slits extending radially inward from the outer cylindrical surface of the piston and extending axially from the distal end of the piston adjacent to the filter to the proximal end of the piston remote from the filter, the slits being circumferentially spaced one from another around the piston and each being adapted to receive a respective anchoring leg of the filter and wherein the slits at their respective proximal ends each communicate with an internal void in the piston so that an anchoring leg received in a respective slit may make contact with at least one other anchoring leg in the internal void.

2. A catheter set as claimed in claim 1, wherein said longitudinal slits extend through part of the length of the retaining member from the distal end thereof and each has a depth increasing from said distal end to accommodate a bent hook at the end of the respective anchoring leg.

3. A catheter set as claimed in claim 1, wherein said second operating member is a tubular member co-axially surrounding an exposed part of the flexible displacement member protruding from the proximal end of the internal catheter and being provided with arresting means for arresting the second operating member in respect of the displacement member.

4. A catheter set as claimed claim 1, wherein the retaining member is formed of metal.

5. A catheter set as claimed in claim 1, wherein the retaining member comprises a cylindrical mounting section coaxial with said cylindrical piston.

6. A catheter set as claimed in claim 5, wherein said slits open to one axial end of the piston.

7. A catheter set as claimed in claim 5, wherein the mounting section and the piston are formed as separate parts bonded together.

8. A catheter set as claimed in claim 5, wherein the slits are formed in said piston by electrical discharge machining.

9. A catheter set as claimed in claim 8, wherein the slits are formed in said piston by wire electrical discharge machining.

10. A catheter set as claimed in claim 5, wherein each anchoring leg has a radially directed hook and wherein the radius of the mounting section is substantially equal to the radial extent of said hook.

11. A catheter set as claimed in any one of claim 1, wherein the slits are formed in said piston by electrical discharge machining.

12. An introduction catheter set for introducing a collapsible, self-expandable implant, said implant being of the type comprising a number of diverging spring-biased anchoring legs to centre the implant in respect of the blood flow through said vessel, the anchoring legs having free ends for engaging said vessel, said catheter set comprising a flexible external guide sheath, a flexible internal catheter having a tubular end member at its distal end and being slidably displaceable inside said guide sheath to a position in which said tubular end member protrudes from the distal end of said sheath, and a retaining member slidably arranged in said tubular end member for releasably retaining the free ends of the anchoring legs of the implant in defined angular positions in respect of each other, said retaining member being connected with a flexible displacement member extending throughout the internal catheter, the proximal ends of said displacement member and the internal catheter being connected with a first and a second operating member, respectively, by operation of which said retaining member is displaceable in respect of said tubular end member from a retaining position, in which the anchoring legs of the implant are inside said tubular end member, to a release position, in which the retaining member protrudes from the tubular end member to release the anchoring legs of the implant, wherein the retaining member comprises a cylindrical piston having a plurality of slits extending radially inward from the outer cylindrical surface of the piston and extending axially from the distal end of the piston adjacent to the filter to the proximal end of the piston remote from the filter, the slits being circumferentially spaced one from another around the piston and each being adapted to receive a respective anchoring leg of the filter and wherein the slits at their respective proximal ends each communicate with an internal void in the piston so that an anchoring leg received in a respective slit may make contact with at least one other anchoring leg in the internal void;

wherein the retaining member comprises a cylindrical mounting section coaxial with said cylindrical piston;

wherein said slits open to one axial end of the piston;

wherein the mounting section and the piston are formed as separate parts bonded together; and wherein each anchoring leg has a radially directed hook and wherein the radius of the mounting section is substantially equal to the radial extent of said hook.

* * * * *